US00PP12316P2

(12) United States Plant Patent
Lamb

(10) Patent No.: US PP12,316 P2
(45) Date of Patent: Jan. 1, 2002

(54) ANTHURIUM PLANT NAMED 'ORANGE CRUSH'

(75) Inventor: Ann E. Lamb, Sebring, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/588,123

(22) Filed: Jun. 2, 2000

(51) Int. Cl.[7] ..... A01H 5/00
(52) U.S. Cl. ..... Plt./365

(58) Field of Search ..... Plt./365, 369

*Primary Examiner*—Bruce R. Campell
*Assistant Examiner*—Kent L. Bell
(74) *Attorney, Agent, or Firm*—Foley & Lardner

(57) ABSTRACT

A new Anthurium plant named 'Orange Crush' particularly distinguished by its bright-orange, heart shaped spathes with an purple-orange spadix; durable spathes that may retain their color for approximately 8 weeks or more; thick, durable, dark-green and shiny foliage with reddish-brown petioles and primary veins; best suited for pot sizes 20 cm and larger.

2 Drawing Sheets

BACKGROUND OF THE INVENTION

This application is copending with U.S. Plant patent application Ser. No. 09/588,124 which is drawn to the sibling cultivar 'Cherry Red'.

The present invention comprises a new and distinct cultivar of Anthurium plant, botanically known as *Anthurium hybrid*, and hereinafter referred to by the cultivar name 'Orange Crush'.

The new cultivar is a product of a planned breeding program, and was obtained from a cross made during such a program in Florida. The female or seed parent was the patented cultivar Anthurium 'Red Hot' (U.S. Plant Pat. No. 9,355). The male or pollen parent was the cultivar Anthurium 'Kozohara' (unpatented).

'Orange Crush' was discovered and selected as a flowering plant within the progeny of the stated cross by the inventor, Ann E. Lamb, in November 1995 in a controlled environment in Florida.

Asexual reproduction of the new cultivar performed by the inventor by division done in Apopka, Fla., and tissue culture done in Sebring, Fla., was used to increase the number of plants for evaluation and has demonstrated that the combination of characteristics as herein disclosed for the new cultivar are firmly fixed and retained through successive generations of asexual reproduction and reproduces true to type.

BRIEF DESCRIPTION OF THE INVENTION

The following traits have been repeatedly observed and are determined to be basic characteristics of 'Orange Crush' which in combination distinguish this Anthurium as a new and distinct cultivar:

1. Plants produce bright-orange, heart-shaped spathes with an orange spadix;

2. Spathes are durable and may retain their color for approximately 8 weeks or more;

3. Foliage is thick, durable, dark-green and shiny with reddish-brown petioles and primary veins; and 4. Plants are best suited for pot sizes 20 cm and larger.

'Orange Crush' has not been observed under all possible environmental conditions. The phenotype of the new cultivar may vary significantly with variations in environment such as temperature, light intensity, and daylength, without any change in genotype.

Of the commercial cultivars known to the present inventor, the most similar in comparison to 'Orange Crush' is the cultivar Anthurium 'Red Hot'. In comparison to 'Red Hot', the spathes of 'Orange Crush' are bright-orange and are longer lasting, larger and more heart-shaped than the spathes of 'Red Hot'. The foliage of 'Orange Crush' is considerably darker-green and more durable than the foliage of 'Red Hot'. Plants of 'Orange Crush' are more tolerant of adverse growing conditions than plants of 'Red Hot'.

The male parental cultivar, Anthurium 'Kozohara' produces large (15 cm) heart-shaped dark red spathes with a white spadix, which are held high above the foliage in the center of the plant. The leaves are light to medium green in color, and the petioles and stems are green. The plant grows best in cool tropical conditions (low 80s day temp, 65 F. night). In comparison, Anthurium 'Orange Crush' produces orange heart-shaped spathes with a purple-orange spadix which are held above the foliage. The leaves of 'Orange Crush' are darker green than those of 'Kozohara', and its stems and petioles are tinged with reddish-brown. Plants of 'Orange Crush' are more tolerant of temperature extremes (high of 104 F., low 55 F.) than are plants of 'Kozohara'.

In comparison to the sibling cultivar 'Cherry Red', 'Orange Crush'produces orange spathes, and 'Cherry Red' produces dark red spathes. Over time, plants of 'Orange Crush' will grow a bit taller and fuller than those of 'Cherry Red'. Overall, the two varieties are similar in appearance, leaf shape and leaf color.

BRIEF DESCRIPTION OF THE DRAWING

The accompanying color photographic illustrations show typical characteristics of 'Orange Crush' grown in a 20-cm pot approximately 16 months after planting a 20-week old liner obtained by tissue culture and grown under appropriate growing conditions, with colors being as nearly true as possible with illustrations of this type.

Sheet 1 is a side view showing the inflorescence and foliage of a plant of 'Orange Crush'.

Sheet 2 is a close-up view of the inflorescence of the instant plant.

DETAILED BOTANICAL DESCRIPTION

The following observations, measurements and values describe plants grown in Apopka, Fla. under greenhouse conditions typical of the horticultural industry in Central Florida. The plants used were 16 months old (4 month old liner+12 months finish time), and were finished in 20 cm pots. All color references are measured against The Royal Horticultural Society (R.H.S.) Colour Chart. Colors are approximate as color depends on horticultural practices such as light level and fertilization rate, among others, without, however, any variance in genotype.

Classification:

*Commercial.*—*Anthurium hybrid* cv. 'Orange Crush'.

Parentage:

*Male parent.*—Anthurium 'Kozohara'.

*Female parent.*—Anthurium 'Red Hot'.

Propagation: Vegetative, by tissue culture.

Plant: Under appropriate growing conditions, plant reaches a size of approximately 55 cm to 62 cm in height from the soil to the top of the leaf canopy, and approximately 74 cm to 80 cm in width after approximately 16 months. The plant has approximately 7 basal branches.

Leaves:

*Form.*—The leaf blade is ovate with a cuspidate tip and a cordate base. The margins are entire. The midrib is straight over the length of the leaf. The leaf margins are flat, having occasional undulations. The leaf blade is rigid and leathery. The upper leaf surface has natural shine and gloss with a polished appearance. Lower leaf surfaces are similarly shiny. All leaves lose gloss as they age.

*Size.*—Leaf blades of a flowering-sized plant are approximately 26 cm to 28.5 cm in overall length and approximately 14 cm to 16.2 cm in width measured at the widest point.

*Veins.*—The veins are sunken. The leaf blade is flat or slightly convex between veins on the upper surface. The midrib protrudes from the upper surface of the leaf for approximately ¾ the length of the leaf. Well defined primary veins radiate out from the juncture of the petiole and the leaf. Veins stand out prominently on the lower side. The midrib is keeled on the lower leaf surface. There are approximately 6 primary veins on the leaf.

*Petiole.*—The petiole is approximately 40 cm to 44 cm in length from the base of the petiole to the base of the leaf blade on the primary shoot. The petiole is approximately 4.0 mm in diameter just below the geniculum. The portion of the petiole beneath the geniculum is straight.

*Petiole sheath.*—The petiole sheath is approximately 5.2 cm in length and approximately 5.0 mm in width at the midpoint. The tip of the petiole sheath is tapered becoming flush with the petiole. There is approximately 32 cm to 36.6 cm between the top of the petiole sheath and the base of the geniculum.

*Geniculum.*—The geniculum is approximately 1.9 cm to 2.5 cm in length, approximately 4.5 mm in diameter, and is often curved. The color is RHS 146A to RHS 146B with RHS 178A to RHS 178B on surfaces exposed to direct light.

*Lobes.*—The leaf has two rounded lobes which extend past the petiole leaf junction. The distance from the petiole/leaf juncture to the highest point on the lobes is approximately 7.8 cm to 8.5 cm.

*Colors.*—Leaf: Upper surface: Greener than, but closest to, RHS 139A. Lower surface: RHS 146B. Midrib: Upper surface: RHS 146B, tinged with RHS 178A. Lower surface: RHS 146B to RHS 146C, tinged with RHS 178B to RHS 178C. Petiole: RHS 146B to RHS 146C, with RHS 178A on surfaces exposed to direct light. Petiole sheath:RHS 146C, tinged with RHS 178B.

Inflorescence:

*Immature.*—The spathe is tightly rolled around the spadix and emerges from the petiole sheath. The spathe is fully open approximately when the peduncle is fully elongated, approximately 60 cm to 65 cm above the soil surface. The color of theinflorescence peduncle is greener than, but closest to, RHS 172A.

*Mature.*—Spathe Color: Fully open: Upper surface: Orange-red, RHS 33A to RHS 33B. Lower surface: Orange-red, RHS 35A to RHS 35B. Faded: Upper surface: RHS 42B to RHS 42C. Lower surface: RHS 35B to RHS 35C.

*Arrangement.*—The inflorescence terminates as a straight wiry peduncle and opens vertically above the leaves.

*Shape.*—The spathe is ovate with a cordate base and a cuspidate tip. It is slightly cupped when first open, flattening with age.

*Size.*—The fully expanded spathe is approximately 9.5 cm to 11.2 cm long and approximately 6.5 cm to 9.0 cm in width (Spathe not flattened for measurement).

*Flowering time.*—After approximately 16 months from a 20-week-old liner, for an untreated plant as illustrated in sheet 1, depending on season, approximately 6 to 8 open blossoms and 5 buds may be present. Smaller blooms may occur on less mature growth. First flowers are typically produced approximately 7 months after planting a 20-week-old liner. Approximately 1–3 flowers are present.

*Lastingness of the individual inflorescence.*—The spathes retain their color for at least 8 weeks before beginning to fade. Cut inflorescences last about 3–4 weeks off the plant.

*Fragrance.*—None.

Reproductive organs:

*Spadix.*—Size: Approximately 5.0 cm to 6.0 cm in length and approximately 6.5 mm in diameter. Color: When the spathe unrolls, the spadix is more orange than, but closest to, RHS 185C to RHS 185D at the base, becoming RHS 42B at the apex. The spadix becomes RHS 148A with age. Number of flowers per spadix: Approximately 150–200. Stamens: Anthers and filaments are minute and not clearly visible. Pollen is white in color. Pistil: Translucent white, protruding between the staminate flowers, firmly fixed to the main axil. The pistil extends approximately 0.5 mm beyond the stamens. There is one pistil per flower.

Roots: White fleshy roots with fine laterals.

Fruit/seeds: Anthurium 'Orange Crush' produces viable pollen and seeds, and has been used as a parent in a plant breeding program. The fruit is an oblong to elliptic berry 7 mm in length, 5 mm in diameter, green 147 C tinged with yellow 20 C when ripe. The flesh of the fruit is translucent yellow/orange 22 B, and is sticky. The seed is elliptic, often somewhat flattened, and is 4 mm in length, and 2 mm in diameter, with a color of 147 C. Each individual berry contains approximately 1 to 2 seeds. Depending on size and degree of pollination, a single inflorescence can yield 150–200 seeds.

Disease resistance: Preventative disease and pest control measures used to grow crops of 'Orange Crush' are typical of ordinary commercial practice. 'Orange Crush' has no sensivity to common pests or pathogens observed to date.

I claim:

1. A new and distinct cultivar of Anthurium plant named 'Orange Crush', as illustrated and described.

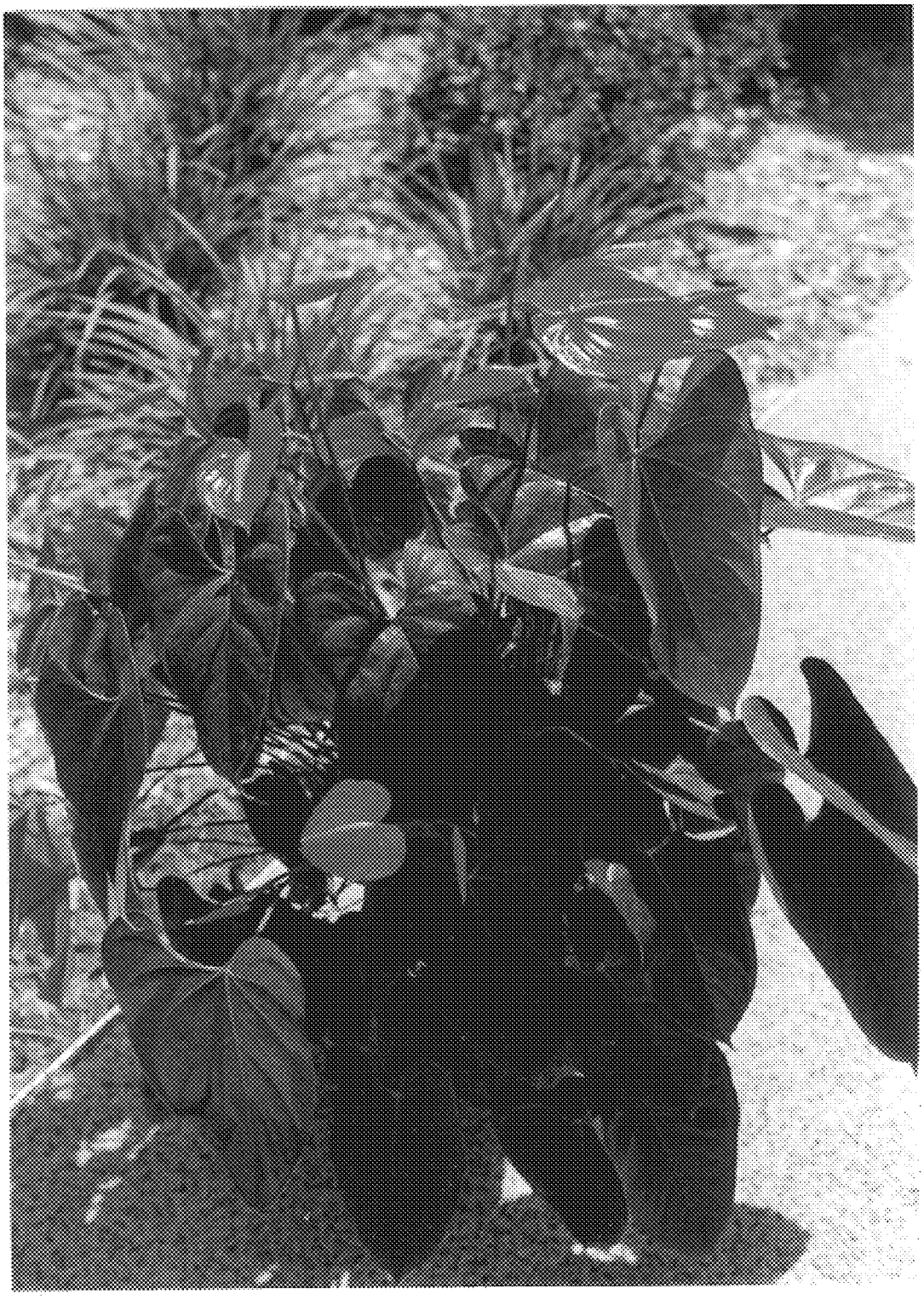

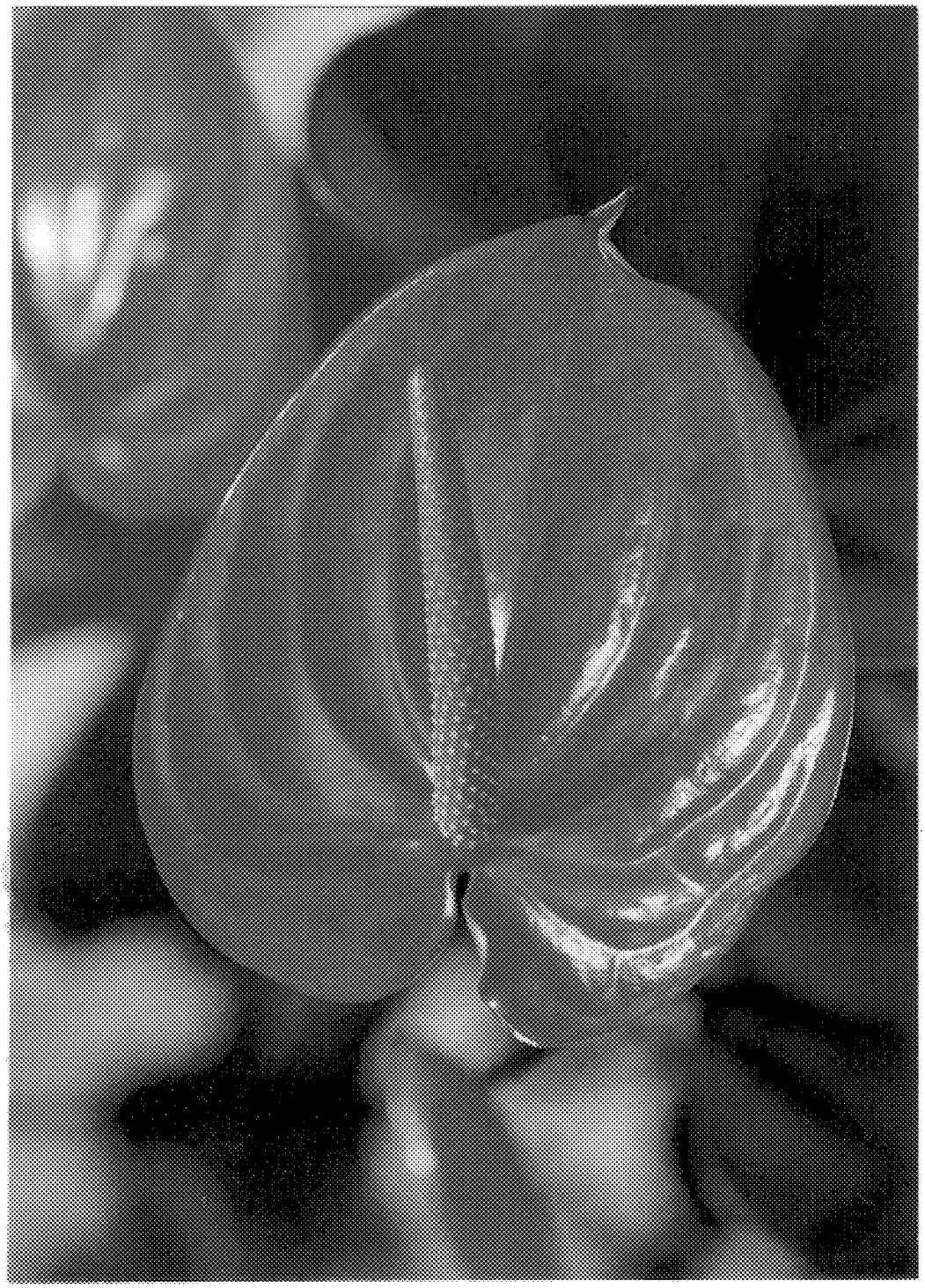

* * * * *